United States Patent
Lei et al.

(10) Patent No.: US 10,485,406 B2
(45) Date of Patent: Nov. 26, 2019

(54) BRONCHOSCOPE ADAPTER AND METHODS FOR USING THE SAME

(71) Applicants: Thomas Dinghua Lei, Mountain View, CA (US); Michael Yuchen Lei, Mountain View, CA (US); Jeffrey Dinghua Lei, Mountain View, CA (US)

(72) Inventors: Thomas Dinghua Lei, Mountain View, CA (US); Michael Yuchen Lei, Mountain View, CA (US); Jeffrey Dinghua Lei, Mountain View, CA (US)

(*) Notice: Subject to any disclaimer, the term of this patent is extended or adjusted under 35 U.S.C. 154(b) by 370 days.

(21) Appl. No.: 14/714,938

(22) Filed: May 18, 2015

(65) Prior Publication Data
US 2015/0335228 A1    Nov. 26, 2015

Related U.S. Application Data

(60) Provisional application No. 62/002,081, filed on May 22, 2014.

(51) Int. Cl.
*A61B 1/00* (2006.01)
*A61M 16/08* (2006.01)
(Continued)

(52) U.S. Cl.
CPC ...... *A61B 1/00137* (2013.01); *A61B 1/00112* (2013.01); *A61B 1/00119* (2013.01);
(Continued)

(58) Field of Classification Search
CPC ............ A61B 1/00112; A61B 1/00114; A61B 1/00117; A61B 1/00119; A61B 1/00121; A61B 1/00124; A61B 1/00126; A61B 1/00128; A61B 1/00131; A61B 1/00137; A61B 1/012; A61B 1/018; A61B 1/267; A61B 1/2673; A61B 1/2676; A61M 5/0463; A61M 5/0486; A61M 39/22;
(Continued)

(56) References Cited

U.S. PATENT DOCUMENTS 4,416,273 A    11/1983  Grimes
4,580,556 A *   4/1986  Kondur ................. A61B 1/267
                                                 128/206.28

(Continued)

FOREIGN PATENT DOCUMENTS

WO    WO03086498 A2    10/2003

OTHER PUBLICATIONS

Finigan et al., Lung cancer screening: past, present and future, Clin Chest Med. Sep. 2013;34(3):365-71.
(Continued)

*Primary Examiner* — Ryan N Henderson
(74) *Attorney, Agent, or Firm* — Payal B. Sud; Bret E. Field; Bozicevic, Field & Francis LLP

(57) ABSTRACT

Bronchoscope adapters and methods of using the same are provided. Aspects of the adaptors include a body having a passageway, a mechanical ventilator access port, a bronchoscope access port configured to receive a bronchoscope into the passageway, and an exit port. The bronchoscope access port comprises a reversibly adjustable inner diameter component that provides locking of the bronchoscope at desired position. The adaptors find use in a variety of different applications.

19 Claims, 6 Drawing Sheets

Cross-Sectional View (Locked)

(51) Int. Cl.
   *A61M 16/04* (2006.01)
   *A61B 1/267* (2006.01)
   *A61B 1/018* (2006.01)
   *A61M 39/22* (2006.01)

(52) U.S. Cl.
   CPC .......... *A61B 1/00128* (2013.01); *A61B 1/018* (2013.01); *A61B 1/2676* (2013.01); *A61M 16/04* (2013.01); *A61M 16/0463* (2013.01); *A61M 39/22* (2013.01)

(58) Field of Classification Search
   CPC .............. A61M 39/221; A61M 39/223; A61M 39/225; A61M 39/227; A61M 39/228; A61M 39/24; A61M 39/26; A61M 39/28; A61M 39/281; A61M 39/283; A61M 39/284; A61M 39/285; A61M 39/286; A61M 39/287; A61M 39/288; A61M 2039/222; A61M 2039/224; A61M 2039/226; A61M 2039/229; A61M 2039/2406; A61M 2039/2413; A61M 2039/2242; A61M 2039/2426; A61M 2039/2433; A61M 2039/244; A61M 2039/2446; A61M 2039/2453; A61M 2039/246; A61M 2039/2466; A61M 2039/2473; A61M 2039/248; A61M 2039/2486; A61M 2039/2493; A61M 2039/261; A61M 2039/262; A61M 2039/263; A61M 2039/265; A61M 2039/266; A61M 2039/267; A61M 2039/268; A61M 2039/282
   USPC ........................ 600/104, 106, 107, 120, 154; 604/164.01–164.13, 167.01–167.06; 128/207.14, 107.16
   See application file for complete search history.

(56) References Cited

U.S. PATENT DOCUMENTS

| | | | |
|---|---|---|---|
| 4,683,879 A | 8/1987 | Williams | |
| 5,009,391 A * | 4/1991 | Steigerwald | A61M 39/0613 137/849 |
| 5,158,569 A | 10/1992 | Strickland et al. | |
| 5,324,271 A * | 6/1994 | Abiuso | A61M 39/0613 604/167.03 |
| 5,752,938 A * | 5/1998 | Flatland | A61B 17/3462 604/167.01 |
| 6,458,103 B1 * | 10/2002 | Albert | A61M 39/0613 604/165.02 |
| 7,473,219 B1 * | 1/2009 | Glenn | A61B 1/00068 600/114 |
| 8,317,149 B2 | 11/2012 | Greenburg et al. | |
| 8,663,088 B2 | 3/2014 | Greenburg et al. | |
| 2001/0021825 A1 * | 9/2001 | Becker | A61M 39/06 604/167.01 |
| 2005/0161048 A1 * | 7/2005 | Rapacki | A61M 16/0463 128/207.14 |
| 2012/0123208 A1 * | 5/2012 | Remmerswaal | A61B 1/018 600/116 |
| 2013/0023729 A1 * | 1/2013 | Vazales | A61B 1/0669 600/104 |

OTHER PUBLICATIONS

Lamprecht et al., Electromagnetic navigation bronchoscopy (ENB): Increasing diagnostic yiel, Respir Med. May 2012:106(5):710-5.
Loo et al., The emerging technique of electromagnetic navigation bronchoscopy-guided fine-needle aspiration of peripheral lung lesions: promising results in 50 lesions, Cancer Cytopathol. Mar. 2014;122(3):191-9.
Musani et al., Advances and future directions in interventional pulmonology, Clin Chest Med. Sep. 2013;34(3):605-10.
Nakajima et al., Early lung cancer: methods for detection, Clin Chest Med. Sep. 2013;34(3):373-83.

* cited by examiner

Cross-Sectional View (Unlocked)

Cross-Sectional View (Locked)

Bird's Eye View

BRONCHOSCOPE ADAPTER AND METHODS FOR USING THE SAME

CROSS-REFERENCE TO RELATED APPLICATIONS

Pursuant to 35 U.S.C. § 119(e), this application claims priority to the filing date of U.S. Provisional Application Ser. No. 62/002,081 filed May 22, 2014, the disclosure of which is herein incorporated by reference.

INTRODUCTION

Bronchoscopy is one of the most common surgical procedures performed by pulmonologists, thoracic surgeons and other trained medical professionals. A fibrotic bronchoscope consists of a long, flexible tube containing several elements: an illumination device for the field distal to the tip of bronchoscope; an image-capturing system delivering a live-video feed with the capability of taking still photos, all through a flexible optical fiber connected to an external light source; and a working channel, via which, both diagnostic and therapeutic instruments, and agents (such as biopsy forceps, aspiration needle, brushes, laser, cryo, radiofrequency probe, fiducial markers, medications, etc.) are inserted or instilled. The distal tip of bronchoscope is steerable on one plane by flipping a lever up and down, and on another plane by rotating the handle of bronchoscope left and right to reach the intended targets.

Bronchoscopies are performed routinely in the diagnosis and treatment of various lung diseases such as pulmonary nodule, lung mass, lung cancer, pneumonia, atelectasis, emphysema and foreign body retrieving. Bronchoscopies are usually performed by pulmonologists, thoracic surgeons, or other trained medical professionals, also known as a bronchoscopist.

One of greatest achievements in pulmonary/chest medicine is the recent development of the electromagnetic navigational bronchoscopy (ENB). The ENB provides tools of high precision in both diagnosis and treatment of pulmonary nodules and lung cancer. The ENB utilizes computer technology in digitalizing the collected image data of a patient's lung anatomy acquired from a chest computerized tomography (CT) scan. It then reconstructs the patient's lung anatomy in a three dimensional model and through an electromagnetic field allows for the physician to locate the intended target (e.g. tumor, nodule, etc.). This new technology, the ENB, revolutionizes the diagnosis and treatment of certain lung diseases. It enables physicians to enter a new frontier of human lung space; it makes it possible to reach peripheral, distal and tiny lesions with high precision in a minimally invasive way compared to conventional bronchoscopy; and it replaces other invasive surgical procedures, such as transthoracic needle biopsy, open lung biopsy, etc.

The nature of the ENB procedure demands high precision, and typically the ENB is performed under general anesthesia. It necessitates the intubation of the patient, an insertion of an endotracheal tube inside the patient's respiratory system while simultaneously placing the patient inside a defined magnetic field. Currently, the ENB requires a minimum staff of four or more: the bronchoscopist, an anesthesiologist, one or more scrub nurses, and a circulating nurse meant solely for the purpose of managing documentations.

During a typical ENB procedure after a patient is intubated and fully anesthetized, the bronchoscopist inserts the bronchoscope into the endotracheal tube via an adapter of three ports, one port for the bronchoscope, one port for the mechanical ventilator, and an exit port for connection to a tracheal tube, e.g., an endotracheal tube. Examples of such adaptors are described in various United States patents, including U.S. Pat. No. 5,158,569 to Strickland, et al.; U.S. Pat. No. 4,683,879 to Tudor; U.S. Pat. No. 4,416,273 to Grimes, et al. After insertion, the procedure moves onto an examination of the general structures of the lungs. Navigation through the lung space is achieved by movement of the bronchoscope handle. The bronchoscope can be pulled up, pushed down, rotated left and right, and flipped by a deflection lever up and down, eventually driving the bronchoscope to the intended target(s). Once the bronchoscope tip reaches its furthest point (either limited by the diameter of the patient's bronchial tree and/or the angle of the bronchial tree branch), an extended working channel/catheter (EWC) along with locatable guide (LG) in place is introduced through the bronchoscope work channel. This EWC and LG have much smaller diameters and far more flexible tips, allowing the physician to overcome the size and angular limitations of the bronchoscope. The EWC and LG extend the physician's reach to the much more distal portions of the bronchial tree and its smaller lesions where the target of interest typically resides. This predetermined navigational path is chosen by a combination of computer software and the expertise of the bronchoscopist. The navigation is accomplished by viewing both live and visual images in a three-dimensional space. Once the tip of LG reaches its intended target, the LG is removed and the tools of choice (biopsy forceps, aspiration needle, needle brush, fiducial or such), will be inserted through the EWC to accomplish intended tasks (such as a biopsies of the lesion or the placement of the fiducial, etc.). The EWC is being held steady and locked at the orifice of the working channel on the bronchoscope by existing devices and methods, such as described in "System of accessories for use with bronchoscope" to Greenberg, B et al., U.S. Pat. Nos. 8,663,088; 8,317,149 to Greenburg B. et al. and PCT patent application no, WO 03/086498 entitled "Endoscope Structure and Techniques for Navigation in Branched Structure" to Gilboa.

SUMMARY

Bronchoscope adapters and methods of using the same are provided. Aspects of the adaptors include a body having a passageway, a mechanical ventilator access port, a bronchoscope access port configured to receive a bronchoscope into the passageway, and an exit port configured to connect to an endotracheal tube. The bronchoscope access port comprises a reversibly adjustable inner diameter component. The adaptors find use in a variety of different applications.

The current invention compliments and completes the existing applications, such as described in the introduction section above, to achieve a complete control and lock down of a bronchoscope along with an EWC at the intended target position by a single operator, i.e., the bronchoscopist. While the current devices and methods described by Gilboa and Greenburg are able to lock the EWC with/on bronchoscope, the bronchoscope itself still remains a moving object, due to the respiration of the patient, the respiration of the bronchoscopist and the repeated maneuvers at the orifice of the EWC; such as changes of instruments, repeated sampling. All these disturbances displace the EWC tip several millimeters or even centimeters away from the intended target due to the subtle moving up and down of the bronchoscope along/relative to the endotracheal tube. This undesired and inevitable movement of bronchoscope relative to the endotracheal tube with the existing devices, could move the EWC tip far away from the intended target, and completely negates the tremendous effort made to navigate to and then lock the EWC tip at the intended target. This undesired movement causes several problems: missing the target without awareness of operator, resulting in poor precision leading to reduction of the diagnostic yield, or requiring repeated navigation to the same target, increasing in the operational time. This intrinsic imperfection of existing devices is currently remedied by requiring additional personnel to hold the bronchoscope at the junction of endotracheal tube periodically.

The existing practice increases the complexity of an already complicated multi-person procedure that requires delicate coordination between the bronchoscopist and the assistants. Current conditions greatly add to the cost of the operation and more so, often result in missing the intended targets of the procedure that depend on the high precision of the operators.

The current invention, the device and its mechanisms described here, allow for the adjustable locking of the bronchoscope to the endotracheal tube. Embodiments of the invention provide and maintain an airtight sealing of the ventilator system, reduce additional personnel, and give the bronchoscopist total control of navigation, targeting, locking and adjusting the bronchoscope as desired. Embodiments of the invention facilitate and secure the locking of the EWC tip to the intended target leading to greater precision in accomplishing the intended tasks. Embodiments of the current invention also expand and accommodate various size ranges of bronchoscopes as compared with current adapters. Embodiments of the current invention, in combination of existing ENB technology, add a new arsenal in the field of the diagnosis and treatment of pulmonary nodules, particularly early lung cancer. Furthermore, embodiments of the invention aid in the reduction of human error, increase the precision of the bronchoscopic surgical procedures, improve the diagnostic yield of bronchoscopic biopsies, deliver any therapeutic modality, such as fiducial, laser to a more precise target location, and greatly reduce the existing operation cost.

Aspects of the invention include an apparatus and related mechanisms, which secure a bronchoscope at a desired position of choice, and allow for the adjustment and security at new positions at will through a single operator, i.e., the bronchoscopist, and further facilitate the securing of EWC or such at target position as intended.

Adaptors according to embodiments of the invention are configured to protect the delicacy of the fiber optic material used in the flexible fiber optic bronchoscope, while providing secure locking of the bronchoscope. The locking is adjustable and controlled by single operator, the bronchoscopist, and achieved by providing a direct contact of the delicate bronchoscope only with an elastomeric material, such as polymeric material, e.g., a silicone or thermoplastic elastomer (TPE) material. The locking mechanism is accomplished through the manipulation of a cylindrical conduit of the elastomeric material, caused by vertical force controlled by the bronchoscopist.

Embodiments of the current invention are configured to maintain the integrity of the airtight ventilator system while bronchoscopic surgical procedures are being performed. Because of the adjustable nature of the current invention, the size range of bronchoscopes able to be used with a single adaptor is greatly expanded, allowing for smaller pediatric bronchoscopes to be employed with an adaptor also configured to be used with adult sized bronchoscopes.

Embodiments of the current invention provide for the substitution of personnel currently required, to reduce human error, and to streamline the complicated operation. By doing so, embodiments of the current invention significantly reduce the cost of bronchoscopic procedures, e.g., as compared to existing practice.

Embodiments of the current invention provide for an airtight ventilator system at the end of bronchoscopic intervention, by simply plugging the bronchoscope access port using the attached plug at the end of procedure when the bronchoscope is removed from the endotracheal tube, before the patient is successfully extubated. Embodiments of the current invention significantly increase the precision and accuracy of the intended operation—leading to higher diagnostic yields, better therapeutic results through reduction of the variables of human error. Embodiments of the current invention expand the arsenal of tools available to the health care professional in the field of diagnosis and treatment of pulmonary nodule, particularly early lung cancer.

DETAILED DESCRIPTION

Figure 1:
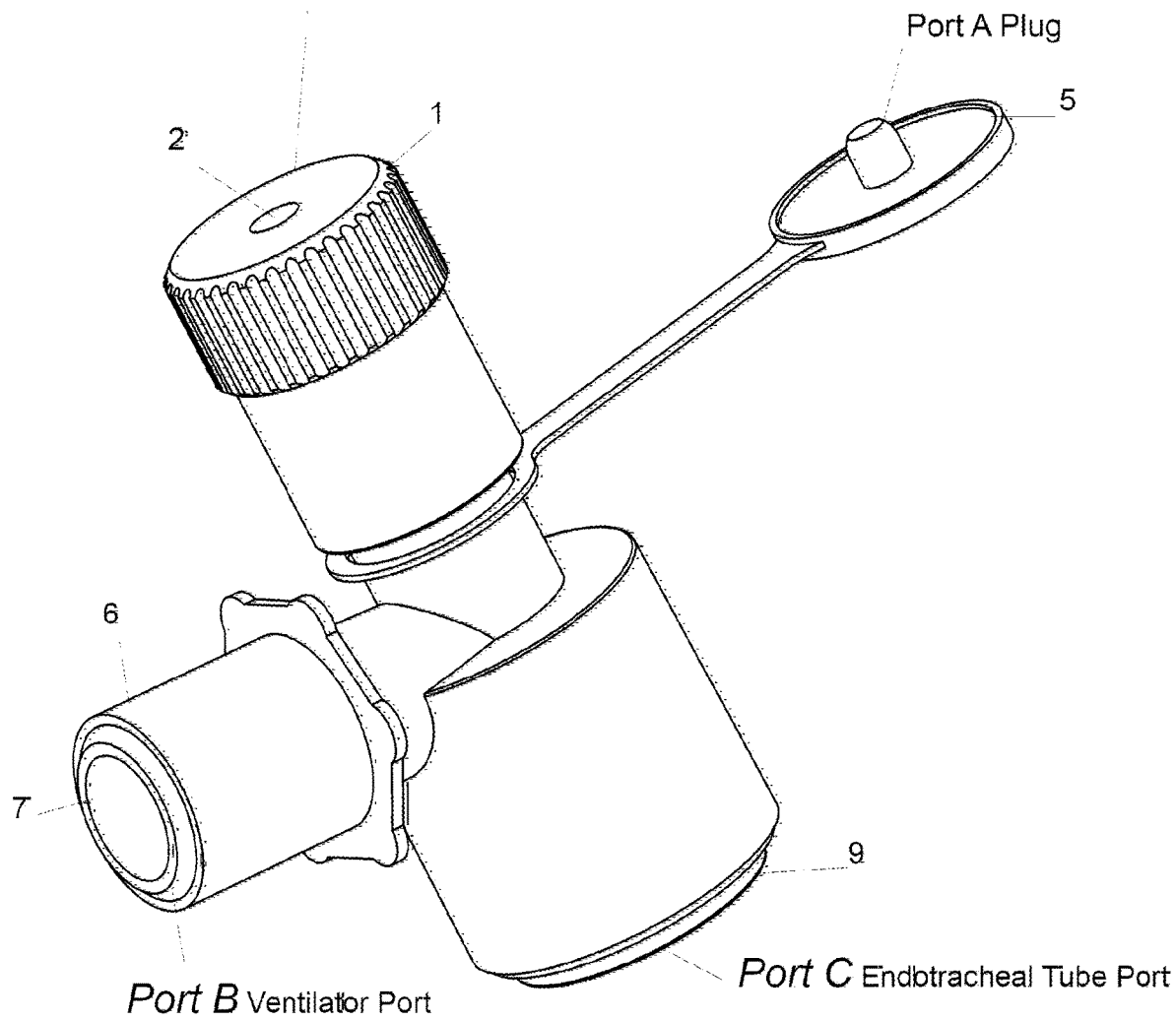
FIGS. 1 to 6 depict various views of a device according to an embodiment of the invention.
Figure 2:
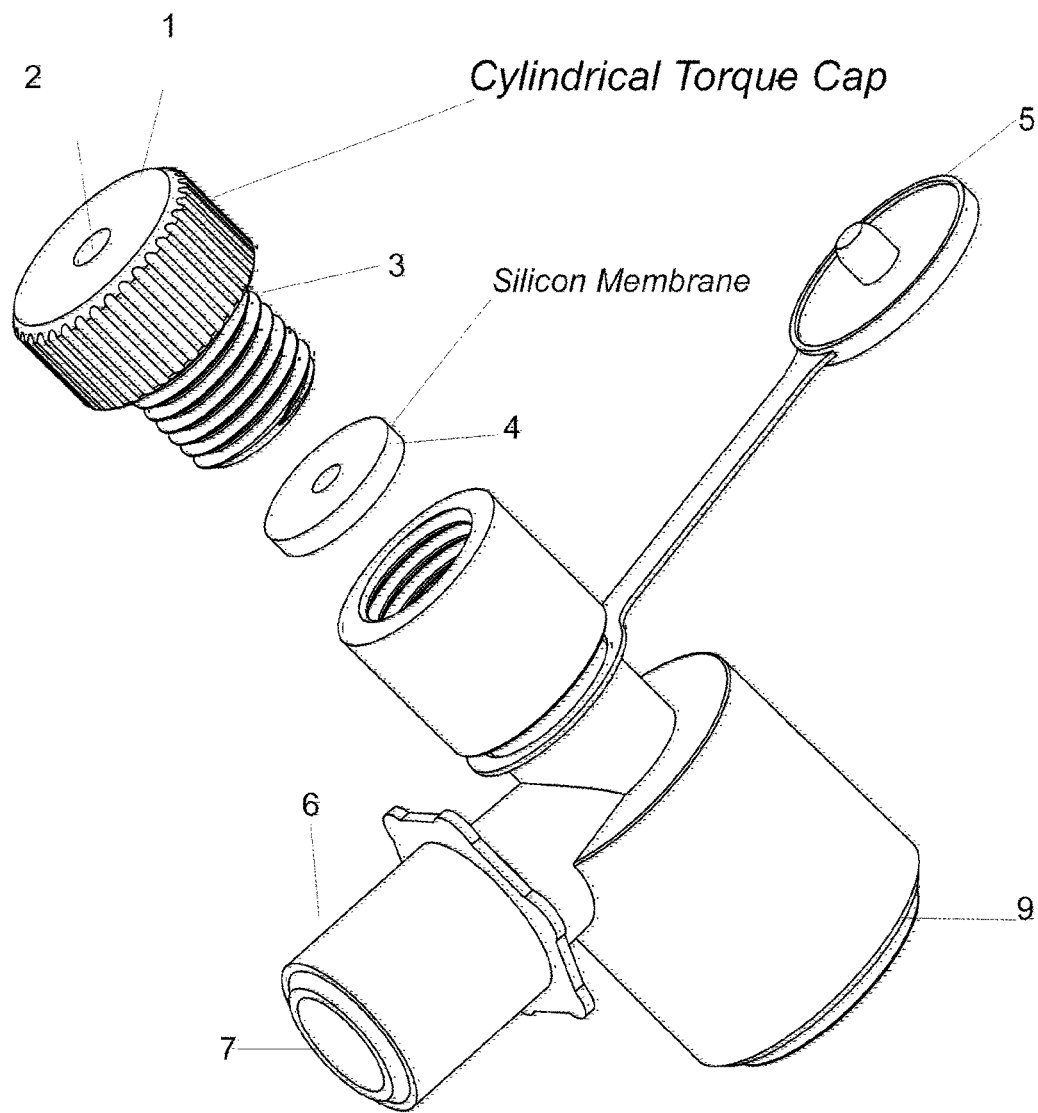
Figure 3:
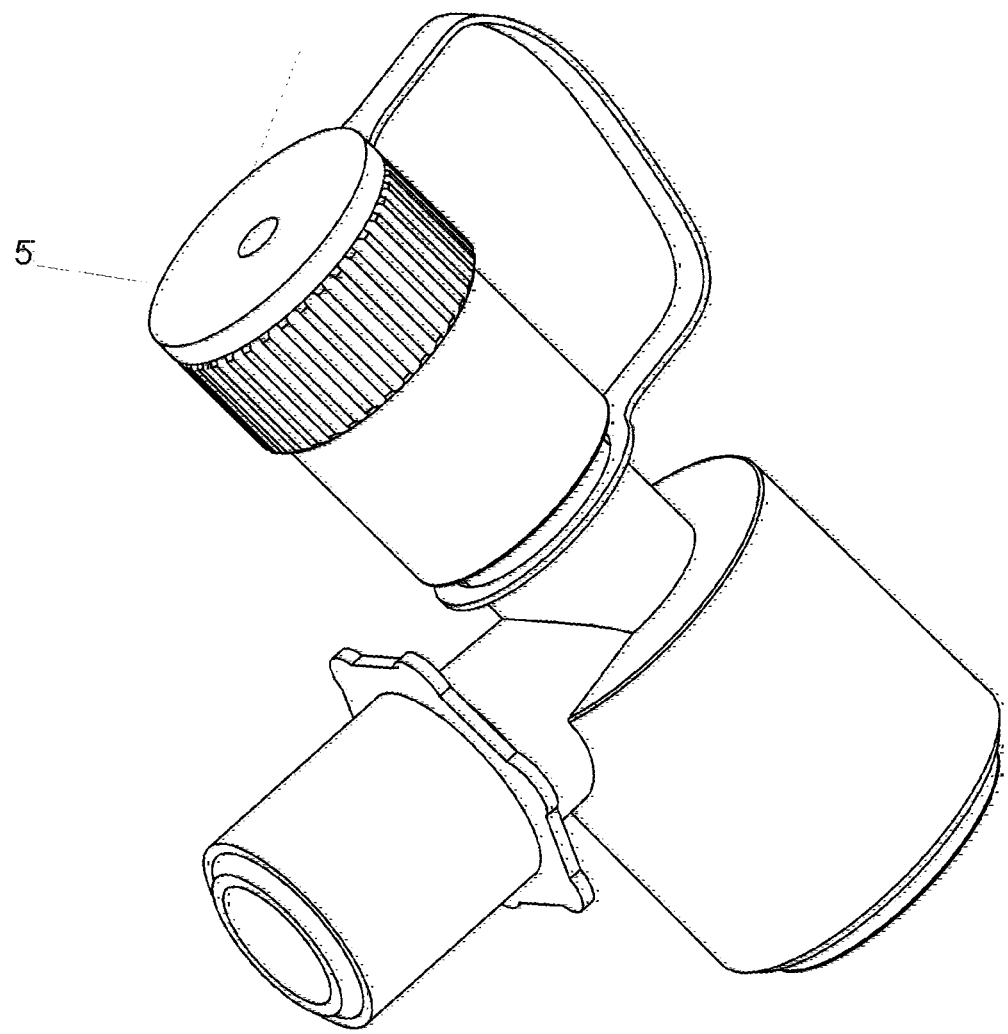

Bronchoscope adapters and methods of using the same are provided. Aspects of the adaptors include a body having a passageway, a mechanical ventilator access port, a bronchoscope access port configured to receive a bronchoscope into the passageway, and an exit port configured to connect to an endotracheal tube. The bronchoscope access port comprises a reversibly adjustable inner diameter component. The adaptors find use in a variety of different applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Bronchoscopy Adaptors

As summarized above, aspects of the invention include a bronchoscopy/mechanical ventilation adaptor. The adaptor is a device that may be viewed as a manifold configured to operationally combine a mechanical ventilator, a bronchoscope and a tracheal tube when these elements are employed in a bronchoscopic procedure. Adaptors as described herein include an elongated body having an internal passageway. The adaptors are dimensioned to be placed on an endotracheal tube that has been placed in the oral cavity of a mammal, such as a human. In some instances, the adaptors have a length ranging from 40 mm to 50 mm, and a width ranging from 35 mm to 55 mm. While the cross-sectional shape of the adaptors may vary, e.g., ranging from square to rectangular to triangular to curvilinear, e.g., circular, in some embodiments the adaptors are tubular in structure. Where the adaptors are tubular in structure, the inner and outer diameters of the adaptors may vary. In some instances, the tubular adaptors have an outer diameter ranging from 12 mm to 25 mm; and an inner diameter ranging from 9 mm to 15 mm. Of course, the dimensions, e.g., inner and/or outer diameters, may vary or be constant in a given adaptor, as desired.

Adaptors of the invention include a bronchoscope access port configured to receive a bronchoscope into the passageway of the adaptor. The bronchoscope access port may be positioned on the body at any convenient location, and in certain embodiments is positioned at one end of the body, e.g., the proximal end of the body of the adaptor. The bronchoscope access port has an inner diameter that is configured to provide access of a bronchoscope into the passageway of the adaptor. While the inner diameter of the bronchoscope access port may vary, in some instances the inner diameter ranges from 3.5 mm to 7 mm, such as 4 to 7 mm. The bronchoscope access port may have a length that varies, ranging in some instances from 10 to 20 mm. While the angle of the longitudinal axis relative to the longitudinal access of the passageway may vary, in some instances ranging from 0 to 15°, in some instances the longitudinal axis of the bronchoscope access port is coaxial with the longitudinal access of the passageway.

Aspects of the adaptors described herein include a reversibly adjustable inner diameter component associated with the bronchoscope access port. A reversibly adjustable inner diameter component is a sub-device of the adaptor that is configured to provide for a reversible change in the inner diameter of the bronchoscope access port. As the change in the inner diameter is reversible, it can be adjusted as desired to accommodate the size of the bronchoscope being used with the adaptor, e.g., to provide a sealing relationship with the bronchoscope and yet not damage the bronchoscope. The reversibly adjustable inner diameter component may be configured to provide a variety of inner diameters, and in some instances is configured to provide a magnitude of diameter change between its most open and most constricted settings that ranges 1 to 3.5 mm, such as 1 to 3.5 mm. The reversibly adjustable inner diameter may be configured to provide for a variety of different inner diameters in the access port, and in some instances has an adjustable diameter that ranges from 4 to 8 mm, such as 3.5 to 7 mm.

The bronchoscope access port comprises may include an actuator that is configured to provide for mechanical adjustment of the reversibly adjustable inner diameter component. Any convenient actuator may be present, so long as it provides for adjustment of the inner diameter of the adjustable component, as desired. An example of an actuator of interest is a compressible member that may be turned in a manner that changes the inner diameter of the adjustable component. In some instances the compressible member, e.g., in the form of a knob or dial, is configured to deform about the longitudinal axis of the bronchoscope access port along a thread so that it moves along the longitudinal axis of the access port and, in doing so, compresses a compressible member, e.g., as described in greater detail below.

The adjustable inner diameter component may include a compressible member configured so that the compression of the compressible member results in a decrease in the inner diameter of the adjustable component. While such a compressible member may have a variety of configurations, in some instances it is configured as a tubular member that rests inside of and is coaxial with the longitudinal axis of the access port. When the compressible member is a tubular member, the dimensions of the compressible member may vary in the compressed and uncompressed states. In some instances, the compressible member in the uncompressed state has a height ranging from 5 to 10 mm, an inner diameter ranging from 5 to 8 mm, such as 3.5 to 7 mm, and an outer diameter that remains constant due to the hard casing enclosing the compressible member. An example of a reversibly adjustable inner diameter component is such a compressible which is operatively coupled or even structurally embedded to a rotatable member, e.g., dial, where rotation of the dial, e.g., along a suitable thread, causes the dial to compress or un-compress the compressible member.

The compressible member of such embodiments may be fabricated from any convenient materials. Materials of interest include elastomeric materials, i.e., materials that are able to resume their original shape when a deforming force is removed. Materials of interest include, but are not limited to, polymeric materials, such as naturally occurring or synthetic rubbers, thermoplastic elastomer (TPE), silicones, etc.

In some instances, the bronchoscope access port may include a sealing mechanism that is configured to seal the access port and passage way connected thereto from the outside environment when a bronchoscope is not present in the access port. The sealing mechanism may vary, and in some instances is configured to provide an airtight seal. Sealing mechanisms of interest include, but are not limited to: plugs, valves, etc., where the sealing mechanism may conveniently be attached to the adaptor whether or not it is sealing the port, if desired.

In addition to the bronchoscope access port, e.g., as described above, adaptors of the invention include a mechanical ventilator access port configured to operatively couple a mechanical ventilator to the passageway of the adaptor. The configuration of the mechanical ventilator access port may vary, so long as it can operatively couple a mechanical ventilator tube to the passageway of the adaptor, e.g., provide for gaseous communication between the interior of the ventilator tube and the passageway of the adaptor. The location of the mechanical ventilator access port may vary on the device, and in some instances is located between the proximal and distal end, e.g., within 15 to 20 mm of the proximal end. In some instances, the mechanical ventilator access port has an inner diameter ranging from 5 to 10 mm, such as 9 to 10 mm. The mechanical ventilator access port may have a length that varies, ranging in some instances from 20 to 25 mm. While the angle of the longitudinal axis of the mechanical ventilator access port relative to the longitudinal access of the passageway may vary, in some instances ranging from 90 to 145, such as 100 to 110°, in some instances the longitudinal axis of the mechanical ventilator access port is orthogonal to the longitudinal access of the passageway. The mechanical ventilator access port may include an attachment element configured to stably associate a ventilator tube with the adaptor, e.g., rotatable in a sealing relationship.

Adaptors of the invention further include an exit port configured to operatively connect the passageway to an endotracheal tube. The configuration of the exit port may vary, so long as it can operatively couple the endotracheal tube to the passageway of the adaptor, e.g., provide for gaseous communication between the passageway of the adaptor and the endotracheal tube and rotatable around the endotracheal tube. The location of the exit port may vary on the device, and in some instances is located at an end of the adaptor, e.g., the distal end. In some instances, the exit port has an inner diameter ranging from 10 to 15, such as 12 to 15 mm. The exit port may have a length that varies, ranging in some instances from 15 to 20 mm. While the angle of the longitudinal axis of the exit port relative to the longitudinal access of the passageway may vary, in some instances ranging from 0 to 15°, in some instances the longitudinal axis of the exit port is coaxial with the longitudinal access of the passageway. The exit port may include an attachment element configured to stably associate a tracheal tube with the adaptor, e.g., in a sealing relationship. The adaptor may be configured to be used with a variety of tracheal tubes, including but not limited to: an endotracheal tube, a tracheostomy tube, etc.

The adaptor may be fabricated from any convenient material. Suitable materials include, but are not limited to: medical grade plastics, thermoplastic elastomer (TPE) or silicones, as well as metals. In some instances, the adaptor is configured as a one time use adaptor, where the material is from which it is fabricated is chosen in terms of suitability for placement close to the oral cavity and outside body (in vitro) of a patient and yet be inexpensive enough to provide for one time use.

The adaptor is a sterile single-use disposable device. Any other similar system using different material and techniques for attaching and locking bronchoscope to endotracheal tube to achieve the similar goal also falls within the scope and spirit of the current invention. Although the current invention is described in the context of electromagnetic navigational bronchoscopy (ENB) in conjunction with mechanic ventilation, endotracheal tube, it applies to any other applications using a bronchoscope with or without involved in endotracheal tube requiring locking the bronchoscope at an adjustable, desired position.

The adaptor having been generally described above, a detailed description of an adaptor according to the embodiment shown in FIG. 1 to FIG. 6 is now provided. It is to be understood that the embodiments shown in FIG. 1 is merely exemplary of the invention which may be embodied in various forms, size using different material. Therefore, the structure and functional specifics, details presented here are not to be interpreted as limiting and excluding, but merely as the basis for the claims, and as representative basis, while the spirit of the current invention could be employed in various forms and shapes, with appropriate structure details.

Figure 4:
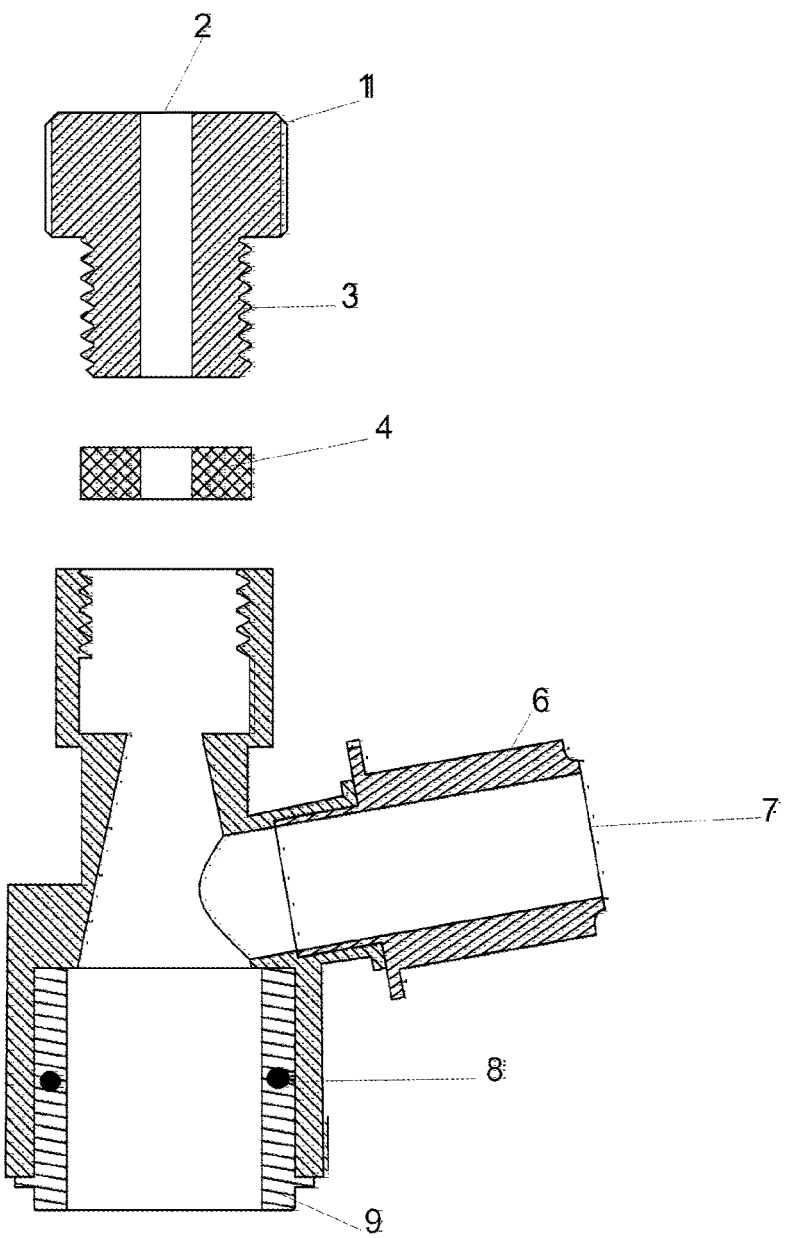
Figure 5:
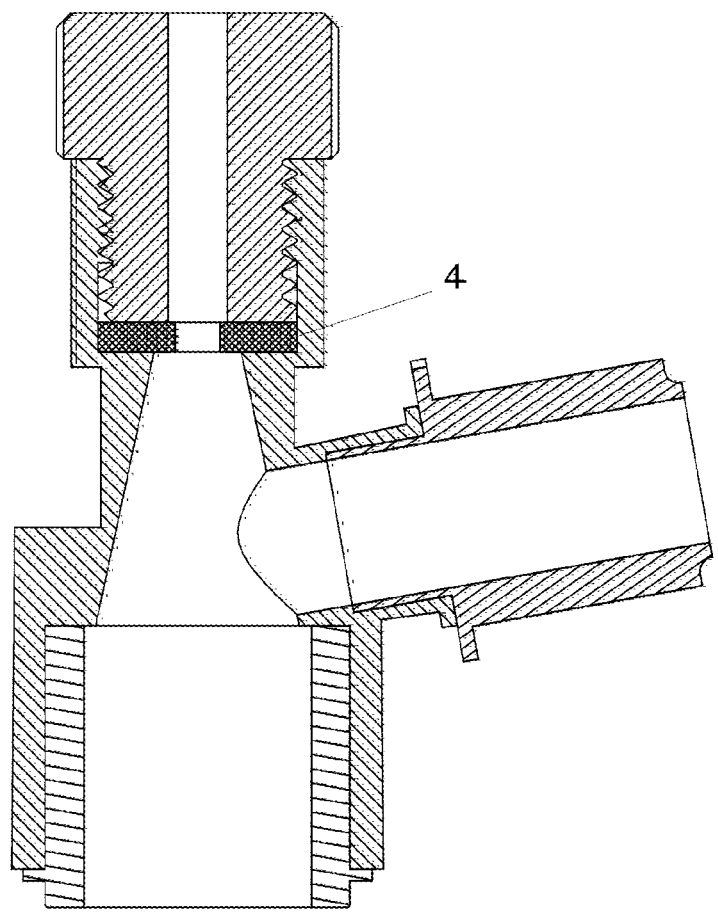
Figure 6:
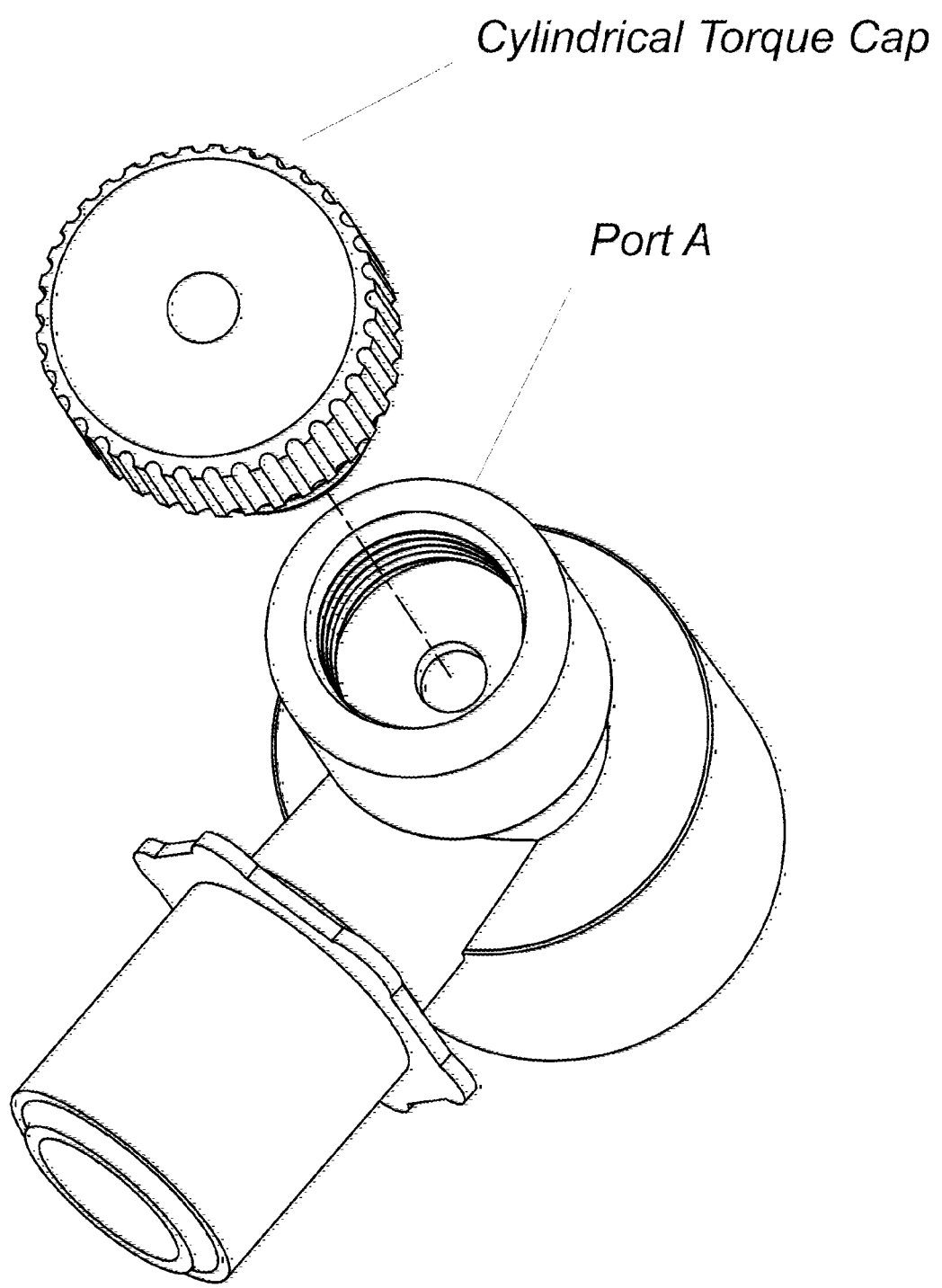

As shown in the FIG. 1 to FIG. 6, the depicted multifunctional bronchoscope/endotracheal tube adapter/manifold is a cylindrical, tubular body, having three ports, i.e., port A, port B and port C. Port B, which is the ventilator port, is at a substantially angular relationship to the longitude body, with outer swivel connecting ventilator machine (not shown). As depicted in FIG. 1, port B includes a one way snap on swivel 6 and ventilator tubing access 7. Port C, which is an endotracheal tube port, includes an inner swivel snap on piece 9 containing an O-ring 8 (as shown in FIG. 4) for seal, connecting an endotracheal tube via access 10 (ETT shown FIG. 5). Port A is the bronchoscope access port. Port A has rigid housing, in which resides an elastomeric, cylindrical compressible member 4 (made of silicone or thermoplastic elastomer TPE) with a through hole fitting various sizes of bronchoscopes. The locking and accommodating mechanism is accomplished through changing this through hole inner diameter by deformation of this silicone/TPE piece 4. Deformation of the piece 4 produces circular pressure against bronchoscope, so to lock it at desired position. The deformation, i.e., the inner diameter, is adjusted by applying and releasing the vertical force from a cylindrical cap/dial 1 containing a through channel, by screwing or torquing the cap up and down along the thread 3 (FIG. 4). The through channel 2 on the access port can be plugged before or after the bronchoscopic procedures using a removable plug 5, in order to maintain the integrity of ventilator circuit.

Methods of Use

Also provided are methods of using adaptors in bronchoscopic procedures, e.g., as described generally above and exemplified in the experimental section, below. In methods of invention, and adaptor having a bronchoscope access port with an adjustable inner diameter component, e.g., as described above, is operatively associated with a tracheal tube that intubates a patient, as well as a mechanical ventilator tube, such that the mechanical ventilator tube is operatively connected to the tracheal tube via the passageway of the adaptor. As desired, a bronchoscope may be introduced into the passageway and then the tracheal tube through the bronchoscope access port, e.g., after removal of a sealing element (such as a plug) from the bronchoscope access port. When desired, the inner diameter of the adjustable inner diameter component may be narrowed, e.g., through compression, to stably associate the bronchoscope with the adaptor, such that the two components do not move relative to other. After any bronchoscope procedure, the inner diameter may be broadened, e.g., through decompression, to release the bronchoscope such that it may be moved with ease relative to the adaptor.

The subject adaptors and methods may be used in a variety of subjects, including humans, e.g., as described above. In certain embodiments, the subjects or patients are humans, ranging from neonates to adults.

Kits

As summarized above, also provided are kits for use in practicing the subject methods. The kits at least include an adaptor, e.g., as described above. The kits may include one or more additional components that may find use in an application where the adaptor is employed, where such additional components include, but are not limited to: extra plugs. The adaptor (and other components when present) of the kits may be present in a suitable container, such as a sterile container, e.g., a sterile pouch.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), Hard Drive etc., on which the information has been recorded. Yet another form of these instructions that may be present is a website address which may be used via the internet to access the information at a removed site.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

EXPERIMENTAL

I. Electromagnetic Navigational Bronchoscopy (ENB) Procedure Using BETLA (Bronchoscope Endotracheal Tube Lock/Adapter)

Patient JD is a 68 years old male with diagnosis of lung nodule/mass, possible early lung cancer. He has two lung nodules, one nodule at right upper lobe, another one at right middle lobe. A diagnostic electromagnetic navigational bronchoscopy is performed on JD as follows. After registration, the patient is transferred from the pre-surgical department to an operating room. An anesthesiologist starts induction of general anesthesia using either inhaled anesthetics, intravenous anesthetics or both if needed. Once the patient is fully sedated, the anesthesiologist intubates the patient by placing of an endotracheal tube into the patient's trachea and connects the endotracheal tube to a mechanical ventilator directly to start mechanical ventilation. The anesthesiologist secures the endotracheal tube by taping it to the patient. Throughout the operation process, the patient's respiration is fully provided by a mechanical ventilator and his vital signs are monitored closely. Once the operation team is ready to start, the anesthesiologist unwraps a single use BETLA, e.g., as depicted in FIG. 1. The anesthesiologist attaches port B, the ventilator port of the BETLA, to a mechanical ventilator. The anesthesiologist attached port C, the endotracheal tube port/connector, to the endotracheal tube, while keeping port A, the bronchoscope port of the BETLA, plugged, awaiting the bronchoscopist to start.

After unplugging port A, a bronchoscopist inserts a bronchoscope into the endotracheal tube via port A of the BETLA. (Because of the inner diameter of port A is adjustable, rather than being fixed as in all current analogous adaptors, the BETLA can accommodate various sizes of bronchoscopes depending on the intended procedures and patients' anatomy). As part of the procedure, the bronchoscopist examines the general structures of patient's lungs, cleans up visible secretions if any, and takes photos for the record. The bronchoscopist navigates along the bronchial tree as if on enclosed highways inside the lung space by performing a variety of manipulations, such as pulling up, pushing down, rotating left and right of the bronchoscope, and flipping the bronchoscope tip by a deflection of the lever up and down, eventually driving the bronchoscope to the nearest point of the intended target(s). The bronchoscopist starts with the right upper lobe lesion, navigates to positions the bronchoscope tip to the nearest point of the intended target(s) according to pre-planned navigational path. This predetermined navigational path is planned and chosen by combining of computer software mapping of airways, targets and the expertise of the bronchoscopist. The navigation process is accomplished with viewing both live and visual images in a three-dimensional fashion. Once the bronchoscope tip reaches its furthest point allowed (either limited by the diameter of the patient's bronchial airway tree and/or the angle of the bronchial tree branch), the bronchoscopist introduces an extended working channel (EWC) with a locatable guide (LG) in place through the bronchoscope work channel. This EWC and LG have much smaller diameters and far more flexible tips, allowing the bronchoscopist to overcome the size and angular limitations of the bronchoscope itself. By using the EWC and LG the bronchoscopist reaches to the smaller, more distal portions of the bronchial tree where the target of interest resides. Once the tip of LG arrives the chosen target, the bronchoscopist locks the bronchoscope at the endotracheal tube by turning the screw/dial on BETLA until the bronchoscope is locked at the desired position, then locks the EWC at the orifice of the working channel on the bronchoscope by existing devices and methods (described in "System of accessories for use with bronchoscope" to Greenberg, B et al., U.S. Pat. Nos. 8,663,088; 8,317,149 to Greenburg B. et al. and PCT patent application no, WO 03/086498 entitled "Endoscope Structure and Techniques for Navigation in Branched Structure" to Gilboa). The bronchoscopist then removes the LG and inserts the tools of choice (biopsy forceps, aspiration needle, needle brush, fiducial or such), through the EWC to accomplish intended tasks (such as a biopsies of the lesion or the placement of the fiducial, etc.). After finishing up the lesion at right upper lobe, the bronchoscopist unlocks both BETLA and EWC/LG, repositions the bronchoscope to navigate to a new target at right middle lobe. This is achieved by loosening up the grip of bronchoscope, and by adjusting the screw/dial on BETLA. A smooth driving up and down till the bronchoscopist reaches the nearest point the bronchoscope allowed to the new target, and repeats the above navigational process with EWC/LG and places the LG tip to the closest point either near or on the new target, completes the intended tasks, e.g., biopsy of the lesion, placing of a fiducial mark. In case there is a need to remove the bronchoscope from the BETLA during procedure or at the end of operation, the bronchoscopist can plug port A of the BETLA to maintain the airtight integrity of ventilation system, to continue providing mechanical ventilation until the patient is awake, and it is safe for the patient to be extubated to breathe on his own.

Using the BETLA is complimentary to existing devices, as the bronchoscopist is able to achieve complete control and maneuver of bronchoscope and EWC, LG through the whole process without the assistance of others, i.e., the bronchoscopist can perform all of these tasks: navigation, positioning, locking of bronchoscope by himself/herself, except passing and receiving tools from supporting staffs. Using the BETLA, the bronchoscopist overcomes a number of sources of mechanical disturbance, such as the respiration of the patient, the respiration of the bronchoscopist and the repeated maneuvers at the orifice of the EWC: changes of instruments, repeated sampling, etc. These undesired and inevitable disturbances and their resulting unintended movements of the bronchoscope, movements or displacements of the EWC tip away from the intended target, etc., can be either completely stopped or significantly minimized by using the BETLA.

Using the BETLA provides and maintains an airtight seal of the ventilator system during and after the operation, reduces the number of personnel required, reduces human errors and gives the bronchoscopist the total control of navigation, targeting, locking and adjusting the bronchoscope, and locking and adjusting the EWC and LG as desired. Use of the BETLA leads to a greater precision in accomplishing the intended tasks, improves the diagnostic yield of bronchoscopic biopsies, delivers therapeutic modality, such as fiducial, laser to a more precise target location, and cuts down the existing operation cost.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A bronchoscopy/mechanical ventilation adaptor, the adaptor consisting of:
    a body ranging in length from 40 to 50 mm and having:
        a first end;
        a second end;
        a passageway extending from the first end to the second end and having a longitudinal axis;
        a mechanical ventilator access port positioned between the first end and the second end of the body configured to operatively couple a mechanical ventilator to the passageway;
        a one way snap on swivel for the mechanical ventilator access port;
        a bronchoscope access port positioned at the first end of the body and comprising an inner surface thread, wherein the bronchoscope access port is configured to receive a bronchoscope into the passageway; and
        an exit port positioned at the second end and configured to operatively connect the passageway to an endo tracheal tube;
    a reversibly adjustable inner diameter component having an adjustable inner diameter that ranges from 3.5 to 7 mm and that is configured to provide a magnitude of inner diameter change ranging from 1 to 3.5 mm, wherein the reversibly adjustable inner diameter component comprises a compressible tube aligned with the longitudinal axis;
    a rotatable cap member consisting of a body having a proximal and distal end, a through channel extending from the proximal end to the distal end and aligned with the longitudinal axis and an outer surface thread at the distal end, wherein the rotatable cap member is engaged with the inner surface thread of the bronchoscope access port and rotates about the longitudinal axis so as to reversibly adjust the inner diameter of the reversibly adjustable inner diameter component; and
    an attached removable plug configured to seal the through channel of the rotatable cap member when a bronchoscope is not present in the bronchoscope access port; and
    an inner swivel snap on piece coupled to the exit port;
    wherein the bronchoscope access port, compressible tube, rotatable cap member through channel and exit port are coaxial with the longitudinal axis of the passageway and the adaptor provides an unobstructed path for the bronchoscope that is coaxial with the longitudinal axis of the passageway.

2. The adaptor according to claim 1, wherein the reversibly adjustable inner diameter component comprises a compressible polymeric material.

3. The adaptor according to claim 2, wherein the polymeric material comprises a silicone or thermoplastic elastomer (TPE).

4. The adaptor according to claim 1, wherein the adaptor is configured to be operatively employed with a mammal.

5. The adaptor according to claim 4, wherein the mammal is a human.

6. The adaptor according to claim 1, wherein the passageway ranges in length from 40 to 50 mm.

7. The adaptor according to claim 1, wherein the mechanical ventilator port has a longitudinal axis that is orthogonal to the longitudinal axis of the passageway.

8. The adaptor according to claim 1, wherein the compressible tube has a height when in an uncompressed state ranging from 5 to 10 mm.

9. The adaptor according to claim 1, wherein a bronchoscope is present in the passageway.

10. A bronchoscopy method, the method comprising:
providing a patient intubated with a tracheal tube operatively coupled to the exit port of an adaptor according to claim 1; and
introducing a bronchoscope into the access port of the adaptor.

11. The method according to claim 10, wherein the method further comprises adjusting the inner diameter of the reversibly adjustable inner diameter component.

12. The method according to claim 10, wherein the method further comprises imaging pulmonary tissue of the patient with the bronchoscope.

13. The method according to claim 10, wherein the method further comprises removing pulmonary tissue from the patient via a working channel of the bronchoscope.

14. The method according to claim 10, wherein the patient is a human.

15. A bronchoscopy/mechanical ventilation adaptor, the adaptor consisting of:
a body ranging in length from 40 to 50 mm and having:
a first end;
a second end;
a passageway extending from the first end to the second end and having a longitudinal axis;
a mechanical ventilator access port positioned between the first end and the second end of the body configured to operatively couple a mechanical ventilator to the passageway;
a one way snap on swivel for the mechanical ventilator access port;
a bronchoscope access port positioned at the first end of the body and comprising a thread, wherein the bronchoscope access port is configured to receive a bronchoscope into the passageway; and
an exit port positioned at the second end and configured to operatively connect the passageway to an endo tracheal tube;
a reversibly adjustable inner diameter component having an adjustable inner diameter that ranges from 3.5 to 7 mm and that is configured to provide a magnitude of inner diameter change ranging from 1 to 3.5 mm, wherein the reversibly adjustable inner diameter component comprises a compressible tube aligned with the longitudinal axis;
a rotatable cap member comprising a through channel aligned with the longitudinal axis and engaged with the thread of the bronchoscope access port,
wherein the rotatable cap member rotates about the longitudinal axis so as to reversibly adjust the inner diameter of the reversibly adjustable inner diameter component; and
an attached removable plug configured to seal the through channel of the rotatable cap member when a bronchoscope is not present in the bronchoscope access port; and
an inner swivel snap on piece coupled to the exit port;
wherein the bronchoscope access port, compressible tube, rotatable cap member through channel and exit port are coaxial with the longitudinal axis of the passageway and further wherein the bronchoscope is present in the passageway and the adaptor provides an unobstructed path for a bronchoscope that is coaxial with the longitudinal axis of the passageway.

16. The adaptor according to claim 15, wherein the reversibly adjustable inner diameter component comprises a compressible polymeric material.

17. The adaptor according to claim 16, wherein the polymeric material comprises a silicone or thermoplastic elastomer (TPE).

18. The adaptor according to claim 15, wherein the passageway ranges in length from 40 to 50 mm.

19. The adaptor according to claim 15, wherein the mechanical ventilator port has a longitudinal axis that is orthogonal to the longitudinal axis of the passageway.

* * * * *